(12) United States Patent
Kadowaki et al.

(10) Patent No.: US 8,338,327 B2
(45) Date of Patent: Dec. 25, 2012

(54) PROCESS FOR PRODUCTION OF ALLYL ACETATE PRODUCTION CATALYST

(75) Inventors: Etsuko Kadowaki, Oita (JP); Wataru Oguchi, Oita (JP); Tetsuo Nakajo, Oita (JP); Yasuhiro Iwama, Oita (JP)

(73) Assignee: Showa Denko K.K., Tokyo (JP)

( * ) Notice: Subject to any disclaimer, the term of this patent is extended or adjusted under 35 U.S.C. 154(b) by 591 days.

(21) Appl. No.: 12/527,363

(22) PCT Filed: Apr. 9, 2008

(86) PCT No.: PCT/JP2008/057388
§ 371 (c)(1),
(2), (4) Date: Aug. 14, 2009

(87) PCT Pub. No.: WO2008/133126
PCT Pub. Date: Nov. 6, 2008

(65) Prior Publication Data
US 2010/0099903 A1    Apr. 22, 2010

(30) Foreign Application Priority Data
Apr. 13, 2007 (JP) .................. 2007-105794

(51) Int. Cl.
*B01J 23/40* (2006.01)
*C07F 3/00* (2006.01)
*C07F 15/00* (2006.01)
*C07F 1/00* (2006.01)

(52) U.S. Cl. ........ 502/326; 556/118; 556/136; 556/138; 556/110

(58) Field of Classification Search .................. None
See application file for complete search history.

(56) References Cited

U.S. PATENT DOCUMENTS

| 3,939,199 A | * | 2/1976 | Fernholz et al. ............ 560/8 |
| 5,948,724 A | * | 9/1999 | Nicolau et al. ............ 502/331 |
| 2001/0012818 A1 | | 8/2001 | Kitchen et al. |
| 2006/0167307 A1 | | 7/2006 | Saihata et al. |

FOREIGN PATENT DOCUMENTS

| EP | 1 112 775 A1 | 7/2001 |
| EP | 1 157 739 A1 | 11/2001 |
| EP | 1 226 868 A1 | 7/2002 |
| WO | 99/21650 A | 5/1999 |
| WO | WO 99/21650 A1 * | 5/1999 |

OTHER PUBLICATIONS

Extended European Search Report issued in corresponding European Patent Application No. 12000689.5 issued May 7, 2012.

* cited by examiner

*Primary Examiner* — Melvin C Mayes
*Assistant Examiner* — Stefanie Cohen
(74) *Attorney, Agent, or Firm* — Sughrue Mion, PLLC

(57) ABSTRACT

An allyl acetate production catalyst comprising at least (a) palladium, (b) gold, (c) a compound containing at least one element selected from copper, nickel, zinc and cobalt, (d) an alkali metal salt compound and (e) a carrier, is produced by a process comprising step 1 in which a homogeneous solution of a palladium-containing compound and a gold-containing compound is supported on a carrier by contact therewith, step 2 in which the carrier obtained in step 1 is contacted with an alkali solution for impregnation, step 3 in which the carrier obtained in step 2 is subjected to reduction treatment, and step 4 in which a compound containing at least one element selected from copper, nickel, zinc and cobalt and an alkali metal salt compound are supported onto the carrier obtained in step 3. The obtained allyl acetate production catalyst has minimal reduction in activity and improved selectivity, when used for production of allyl acetate from propylene, oxygen and acetic acid.

4 Claims, 1 Drawing Sheet

PROCESS FOR PRODUCTION OF ALLYL ACETATE PRODUCTION CATALYST

TECHNICAL FIELD

The present invention relates to a process for production of an allyl acetate production catalyst and to a process for production of allyl acetate using the catalyst. The invention especially relates to a process for production of a catalyst to be used for production of allyl acetate using propylene, oxygen and acetic acid as starting materials, the catalyst comprising (a) palladium, (b) gold, (c) a compound containing at least one element selected from copper, nickel, zinc and cobalt and (d) an alkali metal salt supported on (e) a carrier, as well as a process for production of allyl acetate using the catalyst.

BACKGROUND ART

Allyl acetate is an important industrial starting material used in the production of solvents and allyl alcohol.

Processes for production of allyl acetate include gas phase reactions and liquid phase reactions using propylene, acetic acid and oxygen as starting materials. The known catalysts that are widely used in such reactions contain palladium as the main catalyst component, with alkali metals and/or alkaline earth metal compounds as co-catalyst components, supported on a carrier. For example, Japanese Unexamined Patent Publication HEI No. 2-90145 discloses a process for production of allyl acetate using a catalyst comprising palladium, potassium acetate and copper supported on a carrier.

Other catalyst components have also been investigated, and for example, Japanese Unexamined Patent Publication SHO No. 52-153908 discloses a process for production of allyl acetate using a catalyst with minimal loss of activity by addition of molybdenum in addition to palladium, potassium acetate and copper.

Also, although the reaction differs from that of allyl acetate, Japanese Patent Public Inspection No. 2003-525723 for example, discloses a process for production of a vinyl acetate production catalyst with reduced generation of carbon dioxide during production of vinyl acetate from ethylene, oxygen and acetic acid as the starting material, by supporting palladium in a first step and gold in a second step, carrying out reduction treatment, and then supporting copper(II) acetate and potassium acetate in a third step.

Catalyst technology for production of vinyl acetate has been long established, and it has also been attempted to apply catalyst technology for vinyl acetate production to catalyst technology for production of allyl acetate; however, the journal "Shokubai" [Catalyst], Vol. 33, No. 1 (1991), p. 28-32 reported that the catalyst performance is significantly diminished when the starting material is changed from ethylene to propylene.

DISCLOSURE OF THE INVENTION

It is an object of the present invention to provide an allyl acetate production catalyst with minimal reduction in activity and improved selectivity.

The present inventors have actively conducted research with the goal of solving the problems described above. As a result, we have found that an allyl acetate production catalyst with minimal reduction in activity and improved selectivity can be obtained by using a specific catalyst production process to prepare a catalyst obtained by supporting on a carrier at least palladium, gold, a compound containing at least one element selected from copper, nickel, zinc and cobalt, and an alkali metal salt compound.

The present invention thus relates to the following [1] to [7].

[1] A process for production of an allyl acetate production catalyst comprising (a) palladium, (b) gold, (c) a compound containing at least one element selected from copper, nickel, zinc and cobalt, (d) an alkali metal salt compound and (e) a carrier, the process being characterized by comprising the following steps.

Step 1: A step of preparing a homogeneous solution of a palladium-containing compound and a gold-containing compound, and contacting the solution with the (e) carrier to support both compounds on the carrier.

Step 2: A step of contacting (f) an alkali solution with the carrier obtained in step 1 for impregnation.

Step 3: A step of reduction treatment of the carrier obtained in step 2.

Step 4: A step of supporting (c) a compound containing at least one element selected from copper, nickel, zinc and cobalt and (d) an alkali metal salt compound on the carrier obtained in step 3.

[2] The process for production of an allyl acetate production catalyst according to [1] above, wherein the (c) compound containing at least one element selected from copper, nickel, zinc and cobalt is a compound containing copper or zinc.

[3] The process for production of an allyl acetate production catalyst according to [2] above, wherein the (c) compound containing at least one element selected from copper, nickel, zinc and cobalt is copper acetate.

[4] The process for production of an allyl acetate production catalyst according to any one of [1] to [3] above, wherein the (d) alkali metal salt compound is at least one selected from potassium acetate, sodium acetate and cesium acetate.

[5] The process for production of an allyl acetate production catalyst according to any one of [1] to [4] above, wherein the amount of (b) gold is 1.7-14 parts by mass with respect to 100 parts by mass of the (a) palladium.

[6] A process for production of allyl acetate using propylene, oxygen and acetic acid as starting materials, the process being characterized by using a catalyst produced by a process according to any one of [1] to [5] above.

[7] An allyl acetate production catalyst produced by a process according to any one of [1] to [5] above, wherein the mass ratio of the (a) palladium, the (b) gold, the (c) compound containing at least one element selected from copper, nickel, zinc and cobalt, the (d) alkali metal salt compound is (a):(b):(c):(d)=1:0.00125-22.5:0.02-90:0.2-450.

The process for production of a supported catalyst for allyl acetate production according to the invention can yield a catalyst with minimal reduction in catalyst activity and improved selectivity. Using the catalyst, therefore, allows production costs for allyl acetate to be lowered and therefore permits more efficient production of allyl acetate.

BEST MODE FOR CARRYING OUT THE INVENTION

Figure 1:
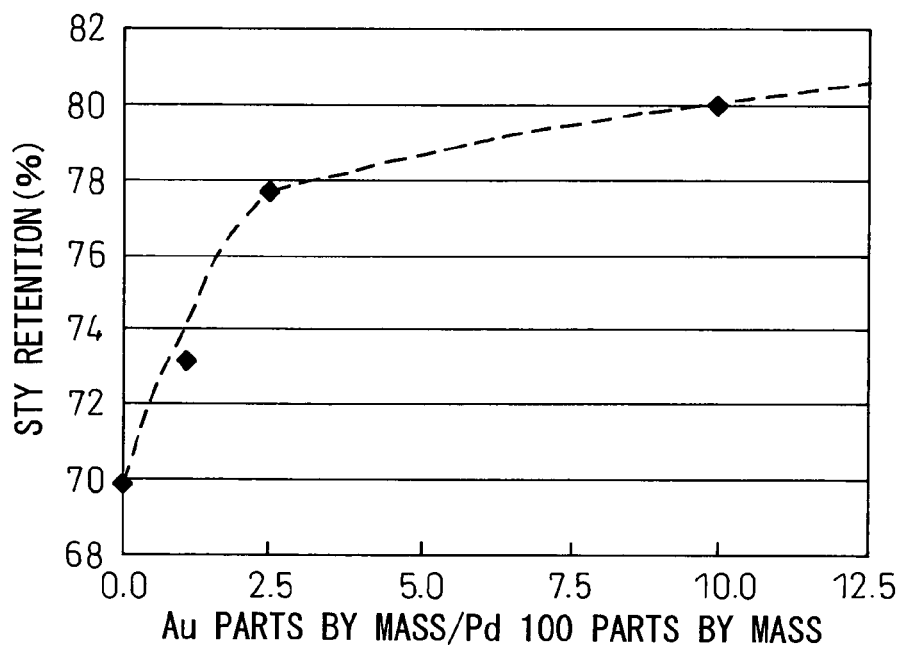
FIG. 1 is a graph showing the relationship between mass ratio of gold with respect to palladium and allyl acetate STY retention, for Examples 11-13 and Comparative Example 6.

Preferred modes of the invention will now be explained in detail with the understanding that the invention is not limited only to these modes, and various applications may be implemented that are within the spirit and scope of the invention.

Catalyst Production Steps

The allyl acetate production catalyst obtained according to the invention comprises the components according to [1] above, and the process for its production comprises the steps according to [1] above. The components and steps will now be explained in detail.

(a) Palladium

According to the invention, the (a) palladium may have any valency but is preferably palladium metal. "Palladium metal" is palladium with a valency of zero. Palladium metal can be usually obtained by reducing divalent and/or tetravalent palladium ion using a reducing agent such as hydrazine or hydrogen, for example. It is not necessary for all of the palladium to be in the metallic state.

There are no particular restrictions on the new-material containing the palladium, i.e. the compound containing elemental palladium. Palladium metal may of course be used, or a palladium precursor that can be converted to palladium metal. As examples of palladium precursors there may be mentioned palladium chloride, palladium nitrate, palladium sulfate, sodium chloropalladate, potassium chloropalladate, barium chloropalladate, palladium acetate and the like, although there is no limitation to these. Sodium chloropalladate is preferred among the above. A palladium precursor may be used as a single compound or a plurality of compounds may be used in combination.

The mass ratio of the (a) palladium and the (e) carrier in the catalyst produced according to the invention is preferably (a):(e)=1:10-1:1000 and more preferably (a):(e)=1:20-1:500. When a palladium precursor is used as the palladium raw material, for example, this ratio is calculated as the mass of palladium element in the palladium precursor used to the mass of the carrier.

(b) Gold

According to the invention, the (b) gold may be supported on the carrier in the form of a compound containing elemental gold, but the preferably the entirety essentially consists of metallic gold. The term "metallic gold" refers to gold with a valency of zero. Metallic gold can usually be obtained by reducing monovalent and/or trivalent gold ion using a reducing agent such as hydrazine or hydrogen. It is not necessary for all of the gold to be in the metallic state.

Also, there are no particular restrictions on the gold raw starting material, i.e. gold-containing compound. Metallic gold may of course be used, or a gold precursor that can be converted to metallic gold. A examples of gold precursors there may be mentioned cloroauric acid, sodium chloroaurate, potassium chloroaurate and the like, although there is no limitation to these. Chloroauric acid is preferred among the above. The gold precursor may be used as a single compound, or a plurality of compounds may be used in combination.

The mass ratio of the (b) gold and the (e) carrier in the catalyst produced according to the invention is preferably (b):(e)=1:40-1:65,000, more preferably (b):(e)=1:550-1:4700, and even more preferably (b):(e)=1:650-1:4000. When a gold precursor is supported as the gold starting material, for example, the ratio is calculated as the mass of gold element in the gold precursor used to the mass of the carrier.

The amount of the (b) gold in the catalyst produced according to the invention is preferably 1.7-14 parts by mass, more preferably 2.0-12 parts by mass and most preferably 2.0-3.5 parts by mass with respect to 100 parts by mass of palladium. The mass ratio referred to here is the mass ratio of gold to elemental palladium. Restricting the amount of gold to within the aforementioned range will allow a satisfactory balance to be achieved between maintaining catalyst activity for the allyl acetate production reaction, and allyl acetate selectivity.

(c) Compound Containing at Least One Element Selected from Copper, Nickel, Zinc and Cobalt.

According to the invention, the (c) compound containing at least one element selected from copper, nickel, zinc and cobalt may be a soluble salt such as a nitric acid salt, carbonic acid salt, sulfuric acid salt, organic acid salt or halide of these elements. Acetic acid salts may be mentioned as organic acid salts. Water-soluble compounds are generally preferred because of their availability. As preferred compounds there may be mentioned copper nitrate, copper acetate, nickel nitrate, nickel acetate, zinc nitrate, zinc acetate, cobalt nitrate and cobalt acetate. Copper acetate is most preferred among the above from the viewpoint of starting material stability and availability. The (c) compound containing at least one element selected from copper, nickel, zinc and cobalt may be a single compound or a combination of two or more compounds.

The mass ratio of the (c) compound containing at least one element selected from copper, nickel, zinc and cobalt and the (e) carrier in the catalyst produced according to the invention is preferably (c):(e)=1:10-1:500 and more preferably (c):(e)=1:20-1:400. When a chloride is supported as the raw material for the compound containing at least one element selected from copper, nickel, zinc and cobalt, for example, the ratio is calculated as the mass of copper, nickel, zinc and cobalt elements in the chloride used to the mass of the carrier.

(d) Alkali Metal Salt Compound

According to the invention, the (d) alkali metal salt compound is preferably at least one compound selected from known alkali metals. Specifically, there may be mentioned hydroxides, acetates, nitrates or hydrogen carbonates of lithium, sodium, potassium, rubidium, cesium and the like. Potassium acetate, sodium acetate and cesium acetate are preferred, and potassium acetate and cesium acetate are more preferred.

The mass ratio of the (d) alkali metal salt compound and the (e) carrier in the catalyst produced according to the invention is preferably (d):(e)=1:2-1:50 and more preferably (d):(e)=1:3-1:40. The ratio is calculated as the mass of the alkali metal salt used to the mass of the carrier.

(e) Carrier

There are no particular restrictions on the (e) carrier used for the invention. It may be any porous substance that is commonly used as a catalyst carrier. Silica, alumina, silica-alumina, diatomaceous earth, montmorillonite, titania and zirconia may be mentioned as preferred examples, with silica being especially preferred. When a carrier composed mainly of silica is used as the carrier, the silica content of the carrier is preferably at least 50 mass % and more preferably at least 90 mass % with respect to the mass of the carrier.

The carrier preferably has a specific surface area (measured by B.E.T.) in the range of 10-1000 $m^2/g$, and more preferably in the range of 100-500 $m^2/g$. The bulk density of the carrier is preferably in the range of 50-1000 g/l and more preferably in the range of 300-500 g/l. The water absorption (described hereunder) of the carrier is preferably 0.05-3 g/g-carrier and more preferably 0.1-2 g/g-carrier. The pore structure of the carrier preferably has a mean pore diameter of 1-1000 nm, and most preferably 2-800 nm. A mean pore diameter of less than 1 nm may interfere with diffusion of gas. A pore diameter of greater than 1000 nm, on the other hand, will result in an excessive small specific surface area of the carrier, potentially reducing the catalytic activity.

The water absorption of the carrier is the numerical value measured by the following method.

1. Approximately 5 g of the carrier is measured out and placed in a 100 cc beaker. This mass is represented as w1.
2. About 15 ml of purified water (ion-exchanged water) is added to the beaker to fully cover the carrier.
3. The mixture is allowed to stand for 30 minutes.
4. The purified water in the supernatant is removed from the carrier.
5. The water adhering to the surface of the carrier is lightly pressed with a paper towel for removal until disappearance of the surface luster.
6. The mass of the carrier+purified water is then measured. This mass is represented as w2.
7. The water absorption of the carrier is calculated by the following formula.

$$\text{Water absorption (g/g-carrier)} = (w2-w1)/w1$$

The amount of water absorption (g) of the carrier is calculated as water absorption (g/g-carrier)×mass (g) of the carrier used.

There are no particular restrictions on the shape of the carrier. Specifically, there may be mentioned powder, globular and pellet forms, although there is no restriction to these. The shape of carrier employed may be selected as optimal for the reactor or the reaction system.

There are also no particular restrictions on the sizes of the carrier particles. When the catalyst is used in a fixed bed tubular reactor for gas-phase reaction and the carrier is globular, the particle diameters are preferably in the range of 1-10 mm and more preferably in the range of 2-8 mm. If the particle diameters are smaller than 1 mm for gas-phase reaction with the catalyst packed into a tubular reactor, a significant pressure loss will be experienced when the gas is passed through, potentially making it impossible to achieve effective gas circulation. If the particle diameters are greater than 10 mm, the reactive gas will not be able to diffuse to the inside of the catalyst, potentially making it impossible for the catalytic reaction to proceed efficiently.

(f) Alkali Solution

There are no particular restrictions on the (f) alkali solution used in step 2, and it may be any solution that is alkaline. As examples of starting materials for alkali solutions there may be mentioned alkaline compounds such as alkali metal or alkaline earth metal hydroxides, alkali metal or alkaline earth metal bicarbonates, alkali metal or alkaline earth metal carbonates and alkali metal or alkaline earth metal silicates. As alkali metals there are preferred lithium, sodium and potassium, and as alkaline earth metals there are preferred barium and strontium. Preferred alkaline compounds among those mentioned above include sodium metasilicate, potassium metasilicate, sodium hydroxide, potassium hydroxide and barium hydroxide. Contact with an alkali solution can convert all or a portion of the palladium compound and all or a portion of the gold compound to oxides or hydroxides.

The alkaline compound is used in moderate excess of the total amount of the (a) palladium and (b) gold. For example, the alkaline compound is used at preferably 1-3 mol and more preferably 1.2-2.5 mol to 1 mol of the (a) palladium. It is also preferably used at 2-10 mol and more preferably 3-8 mol to 1 mol of the (b) gold.

There are no particular restrictions on the solvent for preparation of the alkali solution, but as preferred examples there may be mentioned water, methanol and ethanol.

Each of the steps will now be explained.

Step 1

In this step, a homogeneous solution of a palladium-containing compound and a gold-containing compound is prepared and the solution is contacted with the carrier to support the compounds on the (e) carrier. The compounds are preferably supported on the carrier in an "eggshell-type" state. To obtain an eggshell-type supported catalyst, the method used to load the homogeneous solution of the palladium-containing compound and gold-containing compound on the carrier may be any method that can effectively yield an eggshell-type supported catalyst, without any particular restrictions. An eggshell-type supported catalyst is one type of distribution of an active component (for example, palladium metal) on carrier particles and in a compact, wherein virtually all of the active component is present near the surface of the carrier particles or compact. Specifically, the method may be a method of dissolving the raw compounds in an appropriate solvent such as water or acetone, an inorganic acid or organic acid such as hydrochloric acid, nitric acid or acetic acid, or a solution thereof, for direct supporting on the surface layer of the carrier, or it may be a method of indirect supporting. Methods of direct supporting include impregnation and spray methods. As a method of indirect supporting there may be mentioned a method in which, as described hereunder, a homogeneous solution of the palladium-containing compound and gold-containing compound is first evenly supported onto the carrier (step 1), and then contact impregnation with an (f) alkali solution (step 2) is carried out to cause migration of the palladium-containing compound and gold-containing compound from the inside to the surface, followed by their reduction (step 3).

Supporting of the palladium-containing compound and gold-containing compound onto the carrier can be accomplished by preparing a homogeneous solution of the palladium-containing compound and gold-containing compound and impregnating the carrier with an appropriate amount of the solution. More specifically, the palladium-containing compound and gold-containing compound are dissolved in an appropriate solvent such as water or acetone or in an inorganic acid or organic acid such as hydrochloric acid, nitric acid or acetic acid to prepare a homogeneous solution, after which the carrier is impregnated therewith to obtain an impregnated carrier (A). The impregnation may be followed by drying, but preferably step 2 is carried out next without a drying step in order to simplify the process.

Step 2

This step is a step in which the impregnated carrier (A) obtained in step 1 is contact impregnated with an (f) alkali solution to obtain an impregnated carrier (B).

Since the alkaline substance used in step 2 is liquid it may be used by itself, but preferably it is supplied in the form of a solution. It is preferably water and/or an alcohol solution. There are no particular restrictions on the contact conditions for the impregnated carrier (A) and alkali solution, but the contact time is preferably in the range of 0.5-100 hours and more preferably in the range of 3-50 hours. Sufficient performance may not be obtained with a time of shorter than 0.5 hour, while the carrier may suffer damage if the time is longer than 100 hours.

The contact temperature is not particularly restricted but is preferably in the range of 10-80° C. and more preferably in the range of 20-60° C. Contact at a temperature of below 10° C. may result in an insufficient conversion rate. Also at above 80° C., agglomeration of the palladium and gold may occur. The carrier that has been contact impregnated with the alkali solution obtained in this step is used as the impregnated carrier (B).

Step 3

This is a step in which the impregnated carrier (B) obtained in step 2 is subjected to reduction treatment. The reduction method may be either liquid phase reduction or gas phase reduction. The metal-supported carrier obtained in this step is used as a metal-supported carrier (C).

The reduction reaction is carried out by contacting the impregnated carrier (B) with a reducing agent or its solution. The liquid phase reduction may be carried out in either a non-aqueous or aqueous system using an alcohol or hydrocarbon. The reducing agent used may be a carboxylic acid or its salt, an aldehyde, hydrogen peroxide, a saccharide, a polyhydric phenol, diborane, an amine, hydrazine or the like. As examples of carboxylic acids and their salts there may be mentioned oxalic acid, potassium oxalate, formic acid, potassium formate, ammonium citrate and the like. Glucose may be mentioned as a saccharide. Preferred among the above are hydrazine, formaldehyde, acetaldehyde, hydroquinone, sodium borohydride and potassium citrate, with hydrazine being more preferred.

When reduction is carried out by a liquid phase process, the temperature is not particularly restricted but is preferably in the range of 0-200° C. An even more preferred range is 10-100° C. Contact at a temperature of below 0° C. may result in an insufficient reduction rate. Also at above 200° C., agglomeration of the palladium and gold may occur.

Gas phase reduction is carried out by contacting the impregnated carrier (B) with a reducing gas (reducing agent). The reducing agent used for gas phase reduction is selected from hydrogen, carbon monoxide, alcohol, aldehyde and olefins such as ethylene, propylene and isobutene. Hydrogen and propylene are preferred, however.

The temperature for gas phase reduction is not particularly restricted, but preferably the impregnated carrier (B) is heated to within a range of 30-350° C. An even more preferred range is 100-300° C. A temperature of below 30° C. may result in an insufficient reduction rate, while a temperature of above 300° C. may cause agglomeration of the palladium or gold.

The treatment pressure in gas phase reduction treatment is not particularly restricted but is preferably in the range of 0.0-3.0 MPaG (gauge pressure) from the viewpoint of the equipment that must be used. An even more preferred range is 0.1-1.0 MPaG (gauge pressure).

The supply of reducing gas in the case of gas phase reduction is preferably in a range of 10-15,000 hr$^{-1}$ and most preferably in the range of 100-8000 hr$^{-1}$ as the space velocity (hereinafter abbreviated as SV) under standard conditions.

The gas phase reduction may be carried out with any reducing agent concentration, and if necessary an inert gas may be added as a diluent. As examples of inert gases there may be mentioned helium, argon and nitrogen. The reduction may also be carried out with hydrogen, propylene or the like in the presence of vaporized water.

The catalyst may be packed into the reactor before reduction treatment for reduction with propylene followed by introduction of oxygen and acetic acid to produce allyl acetate.

The reduced carrier may also be washed with water if necessary. The washing may be carried out in a continuous system or a batch system. The washing temperature is preferably in the range of 5-200° C. and more preferably in the range of 15-80° C. There are no particular restrictions on the washing time. Conditions are preferably selected which are sufficient for the purpose of removing residual unwanted impurities. The unwanted impurities in this case might be, for example, sodium or chlorine.

Step 4

This is a step in which (c) a compound containing at least one element selected from copper, nickel, zinc and cobalt and (d) an alkali metal salt compound are supported on the metal-supported carrier (C) obtained in step 3.

The metal-supported carrier (C) is impregnated by contact with a solution containing the necessary amount of the (c) compound containing at least one element selected from copper, nickel, zinc and cobalt and (d) an alkali metal salt compound, at 0.9-1.0 times the amount of the amount of water absorption of the carrier, and then dried to complete supporting of each of the compounds. There are no particular restrictions on the solvent used for this procedure. Any solvent may be used that allows the alkali metal salt compound used to be dissolved with the solution in an amount of 0.9-1.0 times the amount of water absorption of the carrier. However, the solvent is preferably water.

The drying temperature and time are not particularly restricted.

Catalyst Component Composition

The mass ratio of (a), (b), (c) and (d) in the allyl acetate production catalyst obtained by the production process of the invention is preferably (a):(b):(c):(d)=1:0.00125-22.5:0.02-90:0.2-450, more preferably (a):(b):(c):(d)=1:0.017-0.14:0.04-50:0.4-250 and most preferably (a):(b):(c):(d)=1:0.020-0.12:0.04-50:0.4-250. For components (a), (b) and (c) the compositional ratio is for the masses of the elements themselves, and for (d) it is for the mass of the alkali metal salt compound.

The supported masses and compositional ratios of the metal elements in the allyl acetate production catalyst obtained according to the invention may be measured by chemical analysis such as using a high-frequency inductively coupled plasma emission spectrometer (ICP), or by fluorescent X-ray analysis (XRF) or atomic absorption spectrophotometry.

As an example of a measuring method, a prescribed amount of the catalyst is pulverized with a mortar or the like to obtain a uniform powder, and then the catalyst is added to an acid such as hydrofluoric acid or aqua regalis and stirred with heating for dissolution to obtain a homogeneous solution. The solution may then be diluted to an appropriate concentration with purified water and provided for quantitative analysis by ICP.

Production of Allyl Acetate

A process for production of allyl acetate using an allyl acetate production catalyst obtained by the process of the invention will now be explained.

The reaction for production of allyl acetate according to the invention is preferably conducted in a gas phase using propylene, oxygen and acetic acid as the starting materials. The gas phase reaction is not particularly restricted, and any publicly known method using a fixed bed or fluidized bed, for example, may be employed. Preferred for practical advantages is to employ a flow reaction with a fixed bed prepared by packing the catalyst into a corrosion-resistant reaction tube. The reaction formula is as follows.

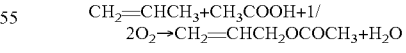

The gas supplied to the reactor contains propylene, oxygen and acetic acid, and if necessary nitrogen, carbon dioxide or a rare gas may be used as a diluent.

The source gas used for the invention is preferably one with a molar ratio selected in the range of acetic acid:propylene:oxygen=1:1-12:0.5-2.

For the reaction to produce allyl acetate, adding water to the reaction system is highly effective for maintaining allyl acetate productivity and the activity of the catalyst. Water vapor is preferably added in a range of 0.5-20 vol % to the gas supplied to the reaction.

High purity propylene is preferably used in the gas supplied to the reactor, but saturated lower hydrocarbons such as methane, ethane and propane may also be included without any particular problem. The oxygen may be diluted with an inert gas such as nitrogen or carbon dioxide gas, and it may be supplied as air, for example, but when the reactive gas is circulated it is advantageous to use oxygen of high concentration, and preferably 99 vol % or greater.

There are no particular restrictions on the reaction temperature. It is preferably in the range of 100-300° C. and even more preferably in the range of 120-250° C. From the standpoint of equipment, it is advantageous in practice for the reaction pressure to be in a range of 0.0-3.0 MPaG (gauge pressure), although this is not restrictive. The pressure is more preferably in the range of 0.1-1.5 MPaG (gauge pressure).

When the reaction is carried out as a flow reaction in a fixed bed, the gas supplied to the reactor is preferably supplied to the catalyst in a range of SV=10-15,000 $hr^{-1}$ and most preferably 300-8000 $hr^{-1}$, under standard conditions.

The present invention will now be explained in greater detail by examples and comparative examples, with the understanding that the invention is in no way limited to the descriptions given below.

Example 1

Production of Catalyst A

A spheroid silica carrier (sphere diameter: 5 mm, specific surface area: 155 $m^2$/g, water absorption: 0.85 g/g-carrier, HSV-I by Shanghai Kaigen, hereinafter referred to as "silica carrier") was used to prepare a catalyst by the following procedure.

Step 1: After mixing 30.3 g of an aqueous sodium chloropalladate solution prepared to a palladium concentration of 19.79 mass % and 6.13 g of an aqueous chloroauric acid solution prepared to a gold concentration of 10 mass %, the mixture was adjusted in volume to 382 ml with purified water to prepare solution A-1. To this there was added 1 L of a silica carrier (bulk density gravity: 473 g/L, amount of water absorption: 402 g/L), for impregnation of the A-1 solution to absorption of the total amount.

Step 2: Purified water was added to 35.6 g of sodium metasilicate nonahydrate for dissolution, and the volume was adjusted to 803 ml to prepare solution A-2. The metal-supported carrier obtained in step 1 was impregnated with solution A-2 and was allowed to stand at room temperature for 20 hours.

Step 3: After adding 26.6 g of hydrazine monohydrate to a slurry of the alkali treated silica carrier obtained in step 2 and gently stirring, it was allowed to stand at room temperature for 4 hours. After filtering the obtained carrier, it was transferred to a stopcock-equipped glass column and subjected to 40 hours of purified water flow for rinsing. It was then dried at 110° C. for 4 hours under an air stream to obtain a metal-supported catalyst (A-3).

Step 4: Purified Water was added to 60 g of potassium acetate and 2.5 g of copper acetate monohydrate for dissolution, and the volume was adjusted to 361 ml. The metal-supported catalyst (A-3) obtained in step 3 was added thereto for absorption of the entire amount. It was then dried at 110° C. for 4 hours under an air stream to obtain an allyl acetate production catalyst A.

Example 2

Production of Catalyst B

Catalyst B was produced by repeating the procedure of Example 1, except that the amount of copper acetate monohydrate was changed from 2.5 g to 7.5 g.

Example 3

Production of Catalyst C

Catalyst C was produced by repeating the procedure of Example 1, except that the 2.5 g of copper acetate monohydrate was changed to 3.0 g of copper nitrate trihydrate.

Example 4

Production of Catalyst D

Catalyst D was produced by repeating the procedure of Example 1, except that the 2.5 g of copper acetate monohydrate was changed to 3.1 g of copper sulfate pentahydrate.

Comparative Example 1

Production of Catalyst E

Step 1: After mixing 30.3 g of an aqueous sodium chloropalladate solution prepared to a palladium concentration of 19.79 mass % and 2.1 g of copper chloride monohydrate, the mixture was adjusted in volume to 382 ml with purified water to prepare solution E-1. To this there was added 1 L of the same silica carrier as used in Example 1 for impregnation of solution E-1 to absorption of the entire amount.

Step 2: Purified water was added to 39.1 g of sodium metasilicate nonahydrate for dissolution, and the volume was adjusted to 803 ml to prepare solution E-2. The metal-supported carrier obtained in step 1 was impregnated with solution E-2 and was allowed to stand at room temperature for 20 hours.

Step 3: After adding 30.0 g of hydrazine monohydrate to a slurry of the alkali treated silica carrier obtained in step 2 and gently stirring, it was allowed to stand at room temperature for 4 hours. After filtering the obtained carrier, it was transferred to a stopcock-equipped glass column and subjected to 40 hours of purified water flow for rinsing. It was then dried at 110° C. for 4 hours under an air stream to obtain a metal-supported catalyst (E-3).

Step 4: Purified water was added to 60 g of potassium acetate for dissolution, and the volume was adjusted to 361 ml. The metal-supported catalyst (E-3) obtained in step 3 was added thereto for absorption of the entire amount. It was then dried at 110° C. for 4 hours under an air stream to obtain an allyl acetate production catalyst E.

Comparative Example 2

Production of Catalyst F

Step 1: A 6.13 g portion of an aqueous chloroauric acid solution prepared to a gold concentration of 10 mass % was adjusted to a volume of 382 ml with purified water to prepare solution F-1. To this there was added 1 L of the same silica carrier as used in Example 1 for impregnation of solution F-1 to absorption of the entire amount.

Step 2: Purified water was added to 3.5 g of sodium metasilicate nonahydrate for dissolution, and the volume was adjusted to 803 ml to prepare solution F-2. The metal-supported carrier obtained in step 1 was impregnated with solution F-2 and was allowed to stand at room temperature for 20 hours.

Step 3: After adding 2.0 g of hydrazine monohydrate to a slurry of the alkali treated silica carrier obtained in step 2 and gently stirring, it was allowed to stand at room temperature for 4 hours. After filtering the obtained carrier, it was transferred to a stopcock-equipped glass column and subjected to 40 hours of purified water flow for rinsing. It was then dried at 110° C. for 4 hours under an air stream to obtain a metal-supported catalyst (F-3).

Step 4: A 30.3 g portion of an aqueous sodium chloropalladate solution prepared to a palladium concentration of 19.79 mass % was adjusted to a volume of 382 ml with purified water to prepare solution F-4. The metal-supported catalyst (F-3) obtained in step 3 was added thereto for impregnation of solution F-4 to absorption of the entire amount.

Step 5: Purified water was added to 32.0 g of sodium metasilicate nonahydrate for dissolution, and the volume was adjusted to 803 ml to prepare solution F-5. The metal-supported catalyst obtained in step 4 was impregnated with solution F-5 and was allowed to stand at room temperature for 20 hours.

Step 6: After adding 24.6 g of hydrazine monohydrate to a slurry of the alkali treated silica carrier obtained in step 5 and gently stirring, it was allowed to stand at room temperature for 4 hours. After filtering the obtained carrier, it was transferred to a stopcock-equipped glass column and subjected to 40 hours of purified water flow for rinsing. It was then dried at 110° C. for 4 hours under an air stream to obtain a metal-supported catalyst (F-6).

Step 7: Purified water was added to 60 g of potassium acetate and 2.5 g of copper acetate monohydrate for dissolution, and the volume was adjusted to 361 ml. The metal-supported catalyst (F-6) obtained in step 6 was added thereto for absorption of the entire amount. It was then dried at 110° C. for 4 hours under an air stream to obtain an allyl acetate production catalyst F.

Example 5

Production of Catalyst G

Step 1: After mixing 30.3 g of an aqueous sodium chloropalladate solution prepared to a palladium concentration of 19.79 mass % and 1.51 g of an aqueous chloroauric acid solution prepared to a gold concentration of 10 mass %, the mixture was adjusted in volume to 382 ml with purified water to prepare solution G-1. To this there was added 1 L of the same silica carrier as used in Example 1 for impregnation of solution G-1 to absorption of the entire amount.

Step 2: Purified water was added to 32.9 g of sodium metasilicate nonahydrate for dissolution, and the volume was adjusted to 803 ml to prepare solution G-2. The metal-supported carrier obtained in step 1 was impregnated with solution G-2 and was allowed to stand at room temperature for 20 hours.

Step 3: After adding 24.9 g of hydrazine monohydrate to a slurry of the alkali treated silica carrier obtained in step 2 and gently stirring, it was allowed to stand at room temperature for 4 hours. After filtering the obtained carrier, it was transferred to a stopcock-equipped glass column and subjected to 40 hours of purified water circulation for rinsing. It was then dried at 110° C. for 4 hours under an air stream to obtain a metal-supported catalyst (G-3).

Step 4: Purified water was added to 33 g of potassium acetate and 7.5 g of copper acetate monohydrate for dissolution, and the volume was adjusted to 361 ml. The metal-supported catalyst (G-3) obtained in step 3 was added thereto for absorption of the entire amount. It was then dried at 110° C. for 4 hours under an air stream to obtain an allyl acetate production catalyst G.

Example 6

Production of Catalyst H

Step 1: After mixing 30.3 g of an aqueous sodium chloropalladate solution prepared to a palladium concentration of 19.79 mass % and 0.77 g of an aqueous chloroauric acid solution prepared to a gold concentration of 10 mass %, the mixture was adjusted in volume to 382 ml with purified water to prepare solution H-1. To this there was added 1 L of the same silica carrier as used in Example 1 for impregnation of solution H-1 to absorption of the entire amount.

Step 2: Purified water was added to 32.5 g of sodium metasilicate nonahydrate for dissolution, and the volume was adjusted to 803 ml to prepare solution H-2. The metal-supported carrier obtained in step 1 was impregnated with solution H-2 and was allowed to stand at room temperature for 20 hours.

Step 3: After adding 24.7 g of hydrazine monohydrate to a slurry of the alkali treated silica carrier obtained in step 2 and gently stirring, it was allowed to stand at room temperature for 4 hours. After filtering the obtained carrier, it was transferred to a stopcock-equipped glass column and subjected to 40 hours of purified water flow for rinsing. It was then dried at 110° C. for 4 hours under an air stream to obtain a metal-supported catalyst (H-3).

Step 4: Purified water was added to 33 g of potassium acetate and 7.5 g of copper acetate monohydrate for dissolution, and the volume was adjusted to 361 ml. The metal-supported catalyst (H-3) obtained in step 3 was added thereto for absorption of the entire amount. It was then dried at 110° C. for 4 hours under an air stream to obtain an allyl acetate production catalyst H.

Comparative Example 3

Production of Catalyst I

Step 1: A 30.3 g portion of an aqueous sodium chloropalladate solution prepared to a palladium concentration of 19.79 mass % was adjusted to a volume of 382 ml with purified water to prepare solution I-1. To this there was added 1 L of the same silica carrier as used in Example 1 for impregnation of solution I-1 to absorption of the entire amount.

Step 2: Purified water was added to 32.1 g of sodium metasilicate nonahydrate for dissolution, and the volume was adjusted to 803 ml to prepare solution I-2. The metal-supported carrier obtained in step 1 was impregnated with solution I-2 and was allowed to stand at room temperature for 20 hours.

Step 3: After adding 24.4 g of hydrazine monohydrate to a slurry of the alkali treated silica carrier obtained in step 2 and gently stirring, it was allowed to stand at room temperature for 4 hours. After filtering the obtained carrier, it was transferred to a stopcock-equipped glass column and subjected to 40 hours of purified water flow for rinsing. It was then dried at 110° C. for 4 hours under an air stream to obtain a metal-supported catalyst (I-3).

Step 4: Purified water was added to 33 g of potassium acetate and 7.5 g of copper acetate monohydrate for dissolution, and the volume was adjusted to 361 ml. The metal-supported catalyst (I-3) obtained in step 3 was added thereto for absorption of the entire amount. It was then dried at 110° C. for 4 hours under an air stream to obtain an allyl acetate production catalyst I.

Examples 7-10, Comparative Examples 4, 5

After uniformly diluting 10.5 ml of each of the catalysts A-F obtained in Examples 1-4 and Comparative Examples 1 and 2 with 31.5 ml of silica carrier, each one was packed into a reaction tube (SUS316 L, inner diameter: 25 mm). Gas with a gas composition of propylene:oxygen:acetic acid:water in a volume ratio of 29:6:7.1:19:38.9 was introduced at a space velocity of 2070 h$^{-1}$ with a reaction temperature of 135° C. and a reaction pressure of 0.8 MPaG (gauge pressure), for reaction to obtain allyl acetate from propylene, oxygen and acetic acid.

Examples 11-13, Comparative Example 6

After uniformly diluting 14.0 ml of each of catalysts B and G-I obtained in Examples 2, 5 and 6 and Comparative Example 3 with 42.0 ml of silica carrier, it was packed into a reaction tube (SUS316 L, inner diameter: 25 mm). Gas with a gas composition of propylene:oxygen:acetic acid:water in a volume ratio of 29:6:7.1:19:38.9 was introduced at a space velocity of 2070 h$^{-1}$ with a reaction temperature of 135° C. and a reaction pressure of 0.8 MPaG (gauge pressure), for reaction to obtain allyl acetate from propylene, oxygen and acetic acid.

Analysis of the reaction products was accomplished by cooling the total amount of the exit gas that had passed through the catalyst-packed layer, collecting the total amount of the condensed reaction solution and performing analysis by gas chromatography. The composition of the non-condensed gas was analyzed by gas chromatography after measuring the total amount of non-condensed gas flowing out during the sampling time and sampling a portion thereof.

Analysis of the condensed reaction mixture was performed by the internal standard method using a GC-14B by Shimadzu Corp., with a FID detector and a TC-WAX capillary column (length: 30 m, inner diameter: 0.25 mm, membrane thickness: 0.25 μm).

Analysis of the non-condensed gas was performed by the absolute calibration curve method, using a GC-14B by Shimadzu Corp. (Shimadzu MGS-4 Gas Chromatography Gas Sampler, equipped with 1 ml measuring tube), with a TCD detector (He carrier gas, current: 100 mA) and a packed column (3 mmϕ×3 m) MS-5A IS (60/80 mesh).

The catalyst activity was calculated as the mass of allyl acetate per hour produced per catalyst volume (liters) (space-time yield: STY, units: g/L-cat·hr).

The allyl acetate selectivity was calculated by the following formula.

Allyl acetate selectivity (based on propylene)(%)=
[allyl acetate production (mol)/amount of propylene consumed (mol)]×100

The results for Examples 7-10, 15 and Comparative Examples 4, 5 are shown in Table 1. The "4 hours" and "50 hours" in Table 1 respectively refer to 4 hours and 50 hours from the start of reaction. Based on Table 1, catalysts A-D of Examples 1-4 had less reduction in allyl acetate activity with time than catalysts E and F of Comparative Examples 1 and 2, and may be considered highly selective catalysts.

TABLE 1

| | | Allyl acetate STY (g/L-cat · hr) | | Allyl acetate selectivity (%) | |
|---|---|---|---|---|---|
| | | 4 hours | 50 hours | 4 hours | 50 hours |
| Example 7 | Catalyst A | 404 | 385 | 80 | 83 |
| Example 8 | Catalyst B | 406 | 395 | 83 | 86 |
| Example 9 | Catalyst C | 423 | 363 | 82 | 85 |
| Example 10 | Catalyst D | 442 | 378 | 81 | 84 |
| Comp. Ex. 4 | Catalyst E | 420 | 351 | 81 | 82 |
| Comp. Ex. 5 | Catalyst F | 393 | 362 | 77 | 80 |
| Example 15 | Catalyst J | 393 | 309 | 80 | 84 |

Figure 2:
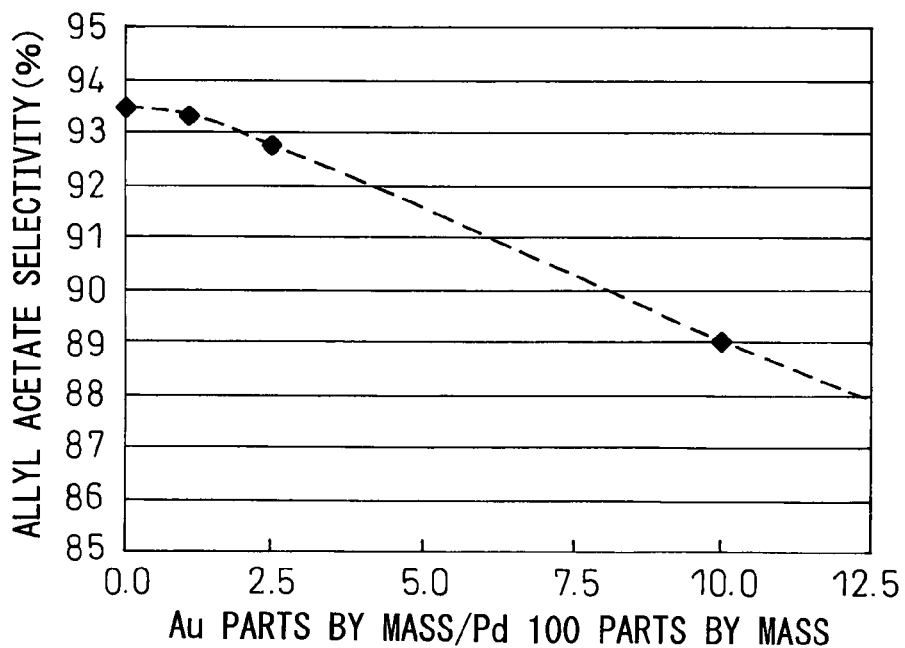
FIG. 2 is a graph showing the relationship between mass ratio of gold with respect to palladium and allyl acetate selectivity, for Examples 11-13 and Comparative Example 6.

The results for Examples 11-13 and Comparative Example 6 are shown in Tables 2 and 3 and in FIGS. 1 and 2. Based on Tables 2 and 3 and FIGS. 1 and 2, catalysts B and G of Examples 11-13 had less reduction in allyl acetate activity with time than catalyst I of Comparative Example 6, while catalysts G and H of Examples 12 and 13 had more excellent allyl acetate selectivity than catalyst B of Example 11. These results demonstrated that catalysts G and H of Examples 12 and 13 have minimal reduction in allyl acetate activity with time and are highly selective catalysts.

TABLE 2

| | | Allyl acetate STY (g/L-cat · hr) | | Allyl acetate selectivity (%) | |
|---|---|---|---|---|---|
| | | 50 hours | 500 hours | 50 hours | 500 hours |
| Example 11 | Catalyst B | 330 | 264 | 89 | 89 |
| Example 12 | Catalyst G | 319 | 248 | 93 | 93 |
| Example 13 | Catalyst H | 284 | 208 | 93 | 93 |
| Comp. Ex. 6 | Catalyst I | 282 | 197 | 92 | 93 |

TABLE 3

| | | Au parts by mass/Pd 100 parts by mass | Allyl acetate STY retention (%) | Allyl acetate selectivity (%) |
|---|---|---|---|---|
| Example 11 | Catalyst B | 10.2 | 80.0 | 89.0 |
| Example 12 | Catalyst G | 2.5 | 77.7 | 92.7 |
| Example 13 | Catalyst H | 1.3 | 73.2 | 93.3 |
| Comp. Ex. 6 | Catalyst I | 0 | 69.9 | 93.5 |

The allyl acetate STY retention was calculated by the following formula.

Allyl acetate STY retention (%)=[allyl acetate STY (g/L-cat·hr) after 500 hours/allyl acetate STY (g/L-cat·hr) after 50 hours]×100

Example 14

Production of Catalyst J

Step 1: After mixing 30.3 g of an aqueous sodium chloropalladate solution prepared to a palladium concentration of 19.79 mass % and 34.3 g of an aqueous chloroauric acid solution prepared to a gold concentration of 10 mass %, the mixture was adjusted in volume to 382 ml with purified water to prepare solution J-1. To this there was added 1 L of the same silica carrier as used in Example 1 for impregnation of solution J-1 to absorption of the entire amount.

Step 2: Purified water was added to 51.8 g of sodium metasilicate nonahydrate for dissolution, and the volume was adjusted to 803 ml to prepare solution J-2. The metal-supported carrier obtained in step 1 was impregnated with solution J-2 and was allowed to stand at room temperature for 20 hours.

Step 3: After adding 35.7 g of hydrazine monohydrate to a slurry of the alkali treated silica carrier obtained in step 2 and gently stirring, it was allowed to stand at room temperature for 4 hours. After filtering the obtained carrier, it was transferred to a stopcock-equipped glass column and subjected to 40 hours of purified water flow for rinsing. It was then dried at 110° C. for 4 hours under an air stream to obtain a metal-supported catalyst (J-3).

Step 4: Purified water was added to 60 g of potassium acetate and 5.1 g of copper acetate monohydrate for dissolution, and the volume was adjusted to 361 ml.

The metal-supported catalyst (J-3) obtained in step 3 was added thereto for absorption of the entire amount. It was then dried at 110° C. for 4 hours under air stream to obtain an allyl acetate production catalyst J (Au 57 parts by mass/Pd 100 parts by mass).

Example 15

The reaction for obtaining allyl acetate as described in Examples 7-10 was carried out using catalyst J obtained in Example 14. The results are shown in Table 1.

INDUSTRIAL APPLICABILITY

The invention allows production of allyl acetate production catalysts with minimal reduction in activity and improved selectivity for production of allyl acetate, and is therefore highly useful for industry.

The invention claimed is:

1. A process for production of an allyl acetate production catalyst comprising (a) palladium, (b) gold, (c) a compound containing at least one element selected from copper, nickel, zinc and cobalt, (d) an alkali metal salt compound and (e) a carrier, the process being characterized by comprising the following steps:
    Step 1: A step of preparing a homogeneous solution of a palladium-containing compound and a gold-containing compound, and contacting the solution with the (e) carrier to support both compounds on the carrier;
    Step 2: A step of contacting (f) an alkali solution with the carrier obtained in step 1 for impregnation;
    Step 3: A step of reduction treatment of the carrier obtained in step 2;
    Step 4: A step of supporting (c) a compound containing at least one element selected from copper, nickel, zinc and cobalt and (d) an alkali metal salt compound on the carrier obtained in step 3, and
    wherein the amount of (b) gold is 2.0-3.5 parts by mass with respect to 100 parts by mass of the (a) palladium.

2. The process for production of an allyl acetate production catalyst according to claim 1, wherein the (c) compound containing at least one element selected from copper, nickel, zinc and cobalt is a compound containing copper or zinc.

3. The process for production of an allyl acetate production catalyst according to claim 2, wherein the (c) compound containing at least one element selected from copper, nickel, zinc and cobalt is copper acetate.

4. The process for production of an allyl acetate production catalyst according to claim 1, wherein the (d) alkali metal salt compound is at least one selected from potassium acetate, sodium acetate and cesium acetate.

* * * * *